United States Patent
Choi et al.

(10) Patent No.: US 9,988,274 B2
(45) Date of Patent: Jun. 5, 2018

(54) METHOD FOR CHEMICAL MODIFICATION OF A GRAPHENE EDGE, GRAPHENE WITH A CHEMICALLY MODIFIED EDGE AND DEVICES INCLUDING THE GRAPHENE

(71) Applicant: SAMSUNG ELECTRONICS CO., LTD., Suwon-si, Gyeonggi-do (KR)

(72) Inventors: Won Mook Choi, Hwaseong-si (KR); Byung Hee Hong, Seoul (KR); Jaeyoung Choi, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 234 days.

(21) Appl. No.: 13/766,876

(22) Filed: Feb. 14, 2013

(65) Prior Publication Data

US 2013/0157034 A1    Jun. 20, 2013

Related U.S. Application Data

(62) Division of application No. 12/576,061, filed on Oct. 8, 2009, now Pat. No. 8,398,876.

(30) Foreign Application Priority Data

Jan. 15, 2009   (KR) ........................ 10-2009-0003302

(51) Int. Cl.
| | |
|---|---|
| *B32B 9/00* | (2006.01) |
| *C01B 31/04* | (2006.01) |
| *B82Y 30/00* | (2011.01) |
| *B82Y 40/00* | (2011.01) |
| *C07C 31/125* | (2006.01) |
| *C07C 31/20* | (2006.01) |

(Continued)

(52) U.S. Cl.
CPC ............ *C01B 31/043* (2013.01); *B82Y 30/00* (2013.01); *B82Y 40/00* (2013.01); *C01B 32/186* (2017.08); *C01B 32/194* (2017.08); *C01B 32/23* (2017.08); *C07C 31/125* (2013.01); *C07C 31/20* (2013.01); *C07C 47/02* (2013.01); *C07C 49/12* (2013.01); *C07C 53/128* (2013.01); *C07C 69/22* (2013.01); *C01B 2204/04* (2013.01); *C01B 2204/32* (2013.01); *Y10T 428/24479* (2015.01); *Y10T 428/24802* (2015.01); *Y10T 428/30* (2015.01)

(58) Field of Classification Search
CPC ........................ C01B 31/0438; C01B 2204/00
USPC ............................... 428/408; 423/447.1, 448
See application file for complete search history.

(56) References Cited

U.S. PATENT DOCUMENTS

| | | |
|---|---|---|
| 2003/0044608 A1 | 3/2003 | Yoshizawa et al. |
| 2004/0253820 A1 | 12/2004 | Deheer et al. |

(Continued)

FOREIGN PATENT DOCUMENTS

| | | |
|---|---|---|
| JP | 2003159699 A | 3/2003 |
| JP | 2006272491 A | 12/2006 |

OTHER PUBLICATIONS

Cervantes-Sodi et al., "Edge-functionalized and substitutionally doped graphene nanoribbons: Electronic and spin properties", Physical Review, B77, 2008, pp. 165427-1-165427-13.

*Primary Examiner* — Daniel H Miller
(74) *Attorney, Agent, or Firm* — Cantor Colburn LLP

(57) ABSTRACT

A method for chemical modification of graphene includes dry etching graphene to provide an etched graphene; and introducing a functional group at an edge of the etched (Continued)

graphene. Also disclosed is graphene, including an etched edge portion, the etched portion including a functional group.

7 Claims, 5 Drawing Sheets

(51) Int. Cl.
    *C07C 47/02*     (2006.01)
    *C07C 49/12*     (2006.01)
    *C07C 53/128*     (2006.01)
    *C07C 69/22*     (2006.01)
    *C01B 32/23*     (2017.01)
    *C01B 32/186*     (2017.01)
    *C01B 32/194*     (2017.01)

(56) References Cited

U.S. PATENT DOCUMENTS

| | | |
|---|---|---|
| 2006/0281306 A1 | 12/2006 | Gstrein et al. |
| 2008/0102020 A1 | 5/2008 | Niu et al. |
| 2008/0302759 A1 | 12/2008 | Zhang |
| 2010/0028681 A1* | 2/2010 | Dai et al. ............... 428/408 |

* cited by examiner

METHOD FOR CHEMICAL MODIFICATION OF A GRAPHENE EDGE, GRAPHENE WITH A CHEMICALLY MODIFIED EDGE AND DEVICES INCLUDING THE GRAPHENE

CROSS REFERENCE TO RELATED APPLICATION

This application is a divisional application of U.S. application Ser. No. 12/576,061, filed Oct. 8, 2009, which claims priority to Korean Patent Application No. 10-2009-0003302, filed on Jan. 15, 2009, and all the benefits accruing therefrom under U.S.C. § 119, the contents of which in their entirety are herein incorporated by reference.

BACKGROUND

1. Field

This disclosure relates to a method for chemical modification of a graphene edge, graphene with a chemically modified edge and devices including the graphene.

2. Description of the Related Art

Graphite is an allotropic form of the element carbon having a stacked structure of two-dimensional planar sheets in which carbon atoms are bonded in an extended fused array of hexagonal rings. The layers are stacked parallel to each other in a three-dimensional crystalline long-range order. There are two allotropic forms with different stacking arrangements, hexagonal and rhombohedral. A single layer of the extended fused array is often referred to as graphene.

A plurality of graphene layers is often referred to in the art as graphite. However, for convenience, "graphene" or "a graphene sheet," as used herein, may comprise one or more layers of graphene. A graphene sheet may have advantageous properties different from those of other materials. In particular, electrons may move on the graphene sheet as if they have zero mass. Thus, electrons on the graphene sheet may move at the velocity of light in a vacuum. Electron mobility on a graphene sheet has been observed to be from about 20,000 square centimeters per volt seconds ($cm^2/Vs$) to about 50,000 $cm^2/Vs$. Further, a graphene sheet may exhibit unusual half-integer quantum hall effects for electrons and holes.

Since the electrical properties of a graphene sheet, with a given thickness, may change depending on its crystallographic orientation, the electrical properties of the graphene sheet may be controlled by selecting the crystallographic orientation of the graphene sheet. Thus, devices using a graphene sheet can be designed to have different electrical properties. Further, for some devices or applications, graphene having different physical or chemical properties is desirable. It is therefore desirable to have a process that provides a chemically modified graphene having different physical or chemical properties.

The electrical properties of a graphene sheet may be compared with those of a carbon nanotube ("CNT"), which is known to exhibit metallic or semiconducting properties depending on the chirality and diameter of the CNT. A complicated separation process may be needed in order to take advantage of such metallic or semiconducting properties of CNTs. A graphene sheet may thus have economic advantages over CNTs because the purification process used with synthesized CNTs may be avoided. Thus, graphene sheets may be less expensive than CNTs. Therefore, it may be desirable to use a graphene sheet in carbon-based electrical or electronic devices in place of CNTs.

SUMMARY

Introduction of a functional group at an etched graphene edge modifies the electrical properties of the graphene. The graphene having modified electrical properties may be applied in various devices, such as a sensor, a field effect transistor or the like.

Disclosed herein is, in an exemplary embodiment, a method for chemical modification of graphene, the method including dry etching graphene to provide graphene having an etched edge; and introducing a functional group at the etched graphene edge.

Also disclosed herein is, in an exemplary embodiment, graphene including an etched edge portion, the etched portion including a functional group.

Also disclosed is a device including graphene, the graphene including an etched edge portion, the etched portion including a functional group.

Also disclosed is a graphene sheet, including: a plurality of layers of graphene, wherein a layer of the graphene has an etched edge portion comprising a functional group.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1A:
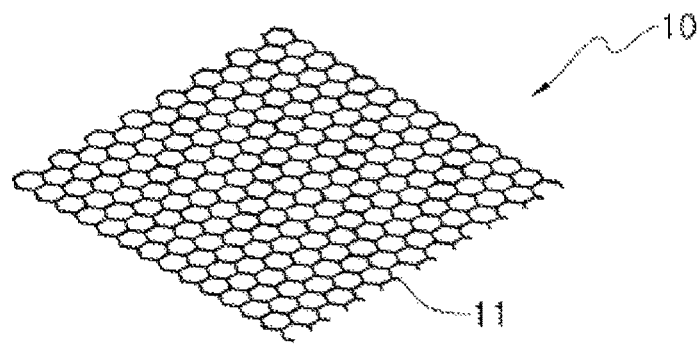
FIGS. 1a to 1f are schematic views illustrating an exemplary embodiment of a process for chemical modification of a graphene edge.

Exemplary embodiments are described more fully hereinafter. The invention may, however, be embodied in many different forms and should not be construed as limited to the exemplary embodiments set forth herein. Rather, these exemplary embodiments are provided so that this disclosure will be thorough and complete, and will fully convey the scope of the invention to those skilled in the art. In the description, details of features and techniques may be omitted to more clearly disclose exemplary embodiments.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. Spatially relative terms, such as "below," "lower," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly. The terminology used herein is for the purpose of describing particular embodiments only and is not intended to be limiting of the invention. As used herein, the singular forms "a," "an" and "the" are intended to include the plural forms as well, unless the context clearly indicates otherwise. Furthermore, the use of the terms a, an, etc. do not denote a limitation of quantity, but rather denote the presence of at least one of the referenced item. The terms "first," "second," and the like do not imply any particular order, but are included to identify individual elements. Moreover, the use of the terms first, second, etc. do not denote any order or importance, but rather the terms first, second, etc. are used to distinguished one element from another. It will be further understood that the terms "comprises" and/or "comprising," or "includes" and/or "including" when used in this specification, specify the presence of stated features, regions, integers, steps, operations, elements and/or components, but do not preclude the presence or addition of one or more other features, regions, integers, steps, operations, elements, components and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Hereinafter, the present invention will be described in detail with reference to the accompanying drawings. However, the aspects, features and advantages of the present invention are not restricted to the ones set forth herein. The above and other aspects, features and advantages of the present invention will become more apparent to one of ordinary skill in the art to which the present invention pertains by referencing a detailed description of the present invention given below.

In the drawings, like reference numerals in the drawings denote like elements. The shape, size and regions, and the like, of the drawing may be exaggerated for clarity.

In this context, a graphene edge refers to a lateral or an end portion of graphene, which is composed of carbon rings.

A graphene edge may be chemically modified by etching graphene at an edge portion and introducing a functional group at the etched graphene edge. Chemical modification of a graphene edge may provide a graphene having different electrical properties than a graphene without the chemical modification. The chemically modified graphene, having modified electrical properties, may be desirably utilized in various devices, such as sensors, field-effect transistors ("FETs") or the like.

In an exemplary embodiment, functional groups are introduced at a graphene edge by dry etching graphene and contacting the etched graphene with a composition capable of providing hydroxide ions.

FIGS. 1a to 1f are schematic views illustrating an exemplary embodiment of a process for chemical modification of a graphene edge. FIG. 1a schematically shows graphene, which is used in an exemplary embodiment. As shown in FIG. 1a, graphene 10, which is to be etched, is first prepared or obtained.

Graphene 10 may comprise fused polycyclic aromatic rings with covalently bonded carbon atoms having $sp^2$ orbital hybridization. The covalently bonded carbon atoms may form a 6-membered ring as a basic repeating unit, but 5- and/or 7-membered rings may also be formed. Graphene may have various structures depending on the content of the 5- and/or 7-membered rings included in the graphene.

Graphene edge 11, i.e., a lateral or an end portion of the graphene, may be generally saturated with hydrogen atoms. In an exemplary embodiment, the graphene edge 11 may be chemically modified by etching the graphene edge and contacting the etched graphene edge with a composition capable of providing hydroxide ions to introduce a functional group at the graphene edge, as is described in further detail below.

In an exemplary embodiment, graphene may be in sheet form. As in a non-limiting exemplary embodiment, the graphene sheet may have a dimension greater than or equal to about 1 millimeter (mm), specifically about 1 mm to about 1,000 mm, more specifically about 10 mm to about 100 mm, along at least one of a transverse direction and a longitudinal direction. The graphene sheet may consist of a single layer of graphene or may comprise multiple layers of graphene (also known as graphite). In an embodiment, the graphene sheet may comprise up to about 300 layers of graphene, specifically up to about 200 layers of graphene, more specifically up to about 100 layers of graphene.

The method for fabricating the graphene used in exemplary embodiments is not particularly restricted. As a non-limiting example, graphene may be formed on a carbonization catalyst, which may be selected so as to obtain a graphene sheet having a large area.

Graphene may be formed on a surface of the carbonization catalyst by various methods. An exemplary method includes a chemical vapor deposition ("CVD") method, wherein a gaseous carbon source is disposed on a carbonization catalyst and heat-treated to form graphene on the carbonization catalyst. In an embodiment, a carbonization catalyst may be formed as a film and placed in a chamber substantially void of oxygen. In an embodiment, a carbonization catalyst comprises an element selected from Ni, Co, Fe, Pt, Au, Al, Cr, Cu, Mg, Mn, Mo, Rh, Si, Ta, Ti, W, U, V, Zr, and the like and a combination thereof. The carbonization catalyst may be the form of a film. The carbonization catalyst film may be either thin or thick. A thin carbonization catalyst film may have a thickness of about 1 nanometer (nm) to about 1,000 nm, specifically about 10 nm to about 700 nm, more specifically about 100 nm to about 500 nm. A thick carbonization catalyst film may have a thickness of about 0.01 mm to about 5 mm, specifically about 0.05 mm to about 2 mm, more specifically about 1 mm. The carbonization catalyst may be put in a chamber, then heat-treatment may be carried out at a temperature of, for example, about 300° C. to about 2,000° C., specifically about 500° C. to about 1,500° C., more specifically about 1,000° C. for a time of about 1 second to about 1 hour, specifically about 1 minute to about 50 minutes, more specifically about 10 minutes while supplying a gaseous carbon source such as carbon monoxide, ethane, ethylene, ethanol, acetylene, propane, butane, butadiene, pentane, pentene, cyclopentadiene, hexane, cyclohexane, benzene, toluene, or the like or a combination thereof at a flow of about 5 standard cubic centimeters per minute (sccm) to about 1,000 sccm, specifically about 10 sccm to about 500 sccm, more specifically about 20 sccm to about 250 sccm, optionally in the presence of an inert gas such as nitrogen, helium, argon, or the like or a combination thereof so as to form graphene. In an embodiment, the gaseous carbon source may consist essentially of carbon monoxide, ethane, ethylene, ethanol, acetylene, propane, butane, butadiene, pentane, pentene, cyclopentadiene, hexane, cyclohexane, benzene, toluene, or the like or a combination thereof. In another embodiment, the gaseous carbon source may consist of carbon monoxide, ethane, ethylene, ethanol, acetylene, propane, butane, butadiene, pentane, pentene, cyclopentadiene, hexane, cyclohexane, benzene, toluene or a combination thereof. The carbon atoms of the carbon source may bond to each other to form a stable fused planar hexagonal shape with an extended pi-electron system, thus forming the graphene sheet. A graphene sheet with a regular lattice structure may be obtained by cooling the produced graphene sheet. In an embodiment the cooling may include natural cooling and the cooling rate may be about 10° C. per minute to about 500° C. per minute, specifically about 20° C. per minute to about 250° C. per minute, more specifically about 30° C. per minute to about 125° C. per minute. Exemplary methods of growing graphene on the carbonization catalyst are not limited to the CVD method.

In another exemplary embodiment, a carbonization catalyst may be contacted with a carbon source such as a liquid carbon-based material. The liquid carbon-based material may be heat-treated in the presence of the carbonization catalyst. In a preliminary heat-treatment of the liquid carbon-based material in the presence of the carbonization catalyst, the liquid carbon-based material may be decomposed by the carbonization catalyst to form carbon. The carbon may be implanted into the carbonization catalyst, and thus be carburized, and a graphene sheet may be formed on the carbonization catalyst. Exemplary processes for contacting the carbonization catalyst with the liquid carbon-based material include immersing or the like. An exemplary liquid carbon-based material is an organic solution. The liquid carbon-based material, however, is not limited to the organic solution and may include any liquid carbon-based material, which may include carbon and be decomposed by the carbonization catalyst. Exemplary organic solutions include polar or non-polar organic solutions having a boiling temperature of about 60° C. to about 400° C., specifically about 70° C. to about 300° C., more specifically about 80° C. to about 250° C. Exemplary organic solutions include an alcohol-based organic solution, an ether-based organic solution, a ketone-based solution, an ester-based organic solution, an organic acid-based organic solution, or the like or a combination comprising at least one of the foregoing organic solutions. In an embodiment, an alcohol-based organic solution or an ether-based organic solution may be used since the alcohol-based organic solution or an ether-based organic solution may be a reducing agent and may a react with and/or adsorb on a carbonization metal catalyst. In the preliminary heat-treatment, the liquid carbon-based material and the carbonization catalyst may be mixed. An exemplary method of mixing is stirring, or the like. In an embodiment, the heat-treatment may be carried out at a temperature of about 100° C. to about 400° C., specifically about 150° C. to about 300° C., more specifically about 200° C. to about 250° C. for a time of about 10 minutes to about 48 hours, specifically about 20 minutes to about 24 hours, more specifically about 40 minutes to about 12 hours.

In another exemplary embodiment, a carbonization catalyst may be contacted with a carbon source, such as a carbon-containing polymer, to form a graphene sheet. The carbon-containing polymer is not limited to a specific carbon-containing polymer. In an embodiment, the carbon-containing polymer is a self-assembling polymer. The self-assembling polymer may be disposed perpendicular to the carbonization polymer and may form a self-assembled layer, which can help formation of a high-density graphene sheet. In an embodiment the self-assembling polymer is at least one polymer selected from the group consisting of an amphiphilic liquid crystal polymer, a conductive polymer and the like.

After the graphene is disposed, the graphene is etched. In an embodiment the graphene is dry etched.

During the etching an etching mask may be used to selectively etch the graphene edge.

Figure 1B:
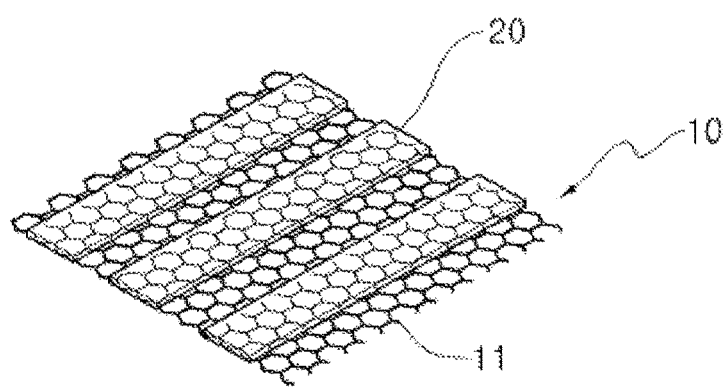

FIG. 1b schematically illustrates an exemplary embodiment wherein graphene is selectively covered by an etching mask.

Referring to FIG. 1b, a portion of the graphene 10 is covered by an etching mask 20 and the graphene 10 is loaded into an etching chamber for dry etching. Then, dry etching may be performed, for example by plasma etching, so as to etch only the graphene edge 11 of the graphene 10.

Dry etching may comprise a physical or chemical etching process in which a plasma of a reactive gas, i.e. a partially ionized gas comprising radicals, ions or an electron beam, is used. The dry etching techniques may be classified as physical etching methods, in which an ion beam or an electron beam is used, and reactive etching methods, in which a chemical reaction occurs. Reactive etching may include chemical etching, such as plasma etching, and physical/chemical etching, such as reactive ion etching ("RIE").

As non-limiting examples of dry etching, dry etching may include etching using an oxygen plasma, RIE using oxygen as a reactive gas, etching using ultraviolet ("UV") light and ozone, or the like or a combination of the foregoing may be used. When oxygen is used as an etching gas, the time for exposing the graphene to the etching gas may be reduced as compared to when ozone is used. In addition to oxygen or ozone, other etching gases, such as a halogen gas or the like, may also be used, but exposure time may be further reduced if oxygen or ozone is used rather than another etching gas.

As a non-limiting example, when oxygen or ozone is used, the dry etching may be carried out by exposing the graphene to about 1 sccm to about 100 sccm, specifically about 10 sccm to about 50 sccm, more specifically about 25 sccm of oxygen or ozone gas under a pressure of about 1 milli-Torr (mTorr) to about 500 mTorr, specifically about 20 mTorr to about 150 mTorr, more specifically about 100 mTorr. Electric power may be about 1 watt (W) to about 500 W, specifically about 20 W to about 100 W, more specifically about 50 W, and exposure time may be about 1 second to about 1000 seconds, specifically about 10 seconds to about 200 seconds, more specifically about 100 seconds. The exposure time may be selected differently depending on the graphene thickness.

Figure 1C:
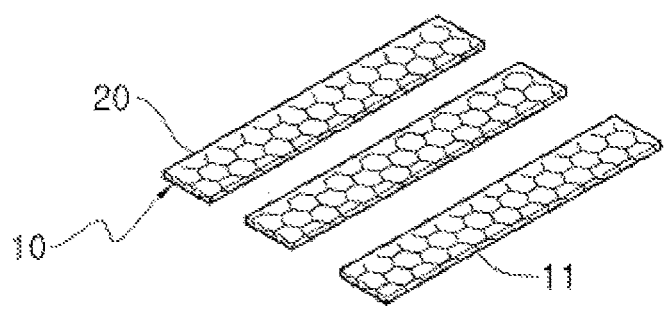

FIG. 1c schematically illustrates graphene after dry etching according to an exemplary embodiment.

Referring to FIG. 1c, the portion not covered by the etching mask 20 is removed by the etching and the end portions of the graphene covered by the mask 20, i.e., the edge portions 11 of graphene are cut by the etching.

Figure 1D:
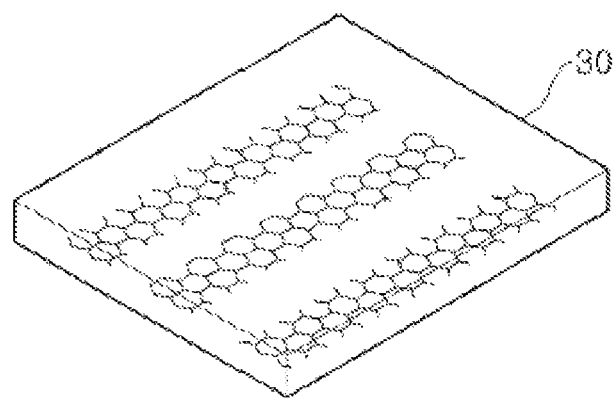

FIG. 1d schematically illustrates an exemplary embodiment of the etched graphene after removing the mask and contacting with a composition capable of providing hydroxide ions.

As shown in FIG. 1d, when the mask is removed from the etched graphene, graphene having a shape, for example, a ribbon shape, or the like, may be obtained. When the graphene, such as a graphene ribbon, is contacted with a composition 30 capable of providing hydroxide ions, a functional group may be introduced at the graphene edge, and, as a result, the graphene may be chemically modified at the edge portion. The contacting may be for a time of about 1 second to about 1 hour, specifically about 1 minute to about 50 minutes, more specifically about 30 minutes. The contacting may be at a temperature of about 25° C. to about 200° C.

The composition 30 is capable of providing hydroxide ions to the graphene edge. In an embodiment, the composition 30 may be a solution. As in a non-limiting example, the composition may comprise water, alcohol, or the like or a combination thereof. In an embodiment, the composition consists essentially of water, alcohol, or the like or a combination thereof. In another embodiment, the composition consists of water, alcohol or a combination thereof. In an embodiment, the composition 30 is steam.

Figure 1E:
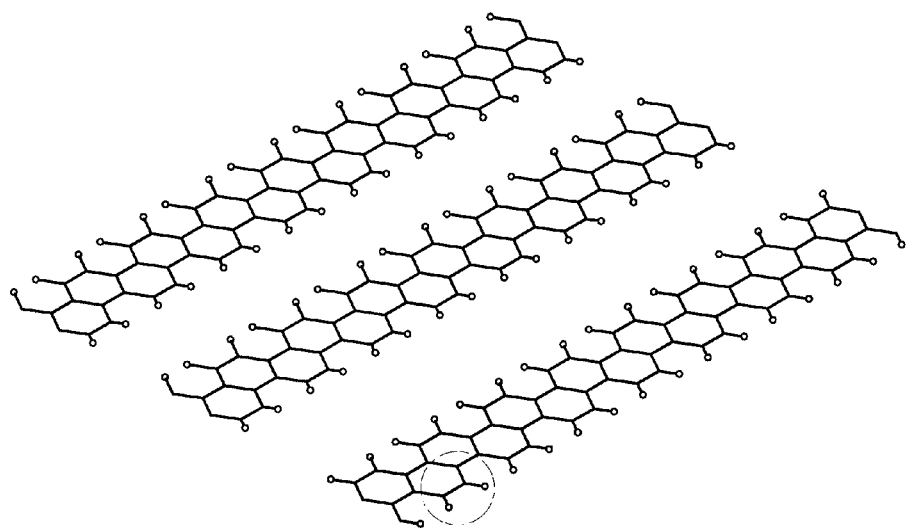

FIG. 1e schematically illustrates the graphene in which a functional group, specifically a plurality of functional groups s are introduced at the edge portion according to an exemplary embodiment. The edge portion is also shown enlarged in FIG. 1f.

Figure 1F:
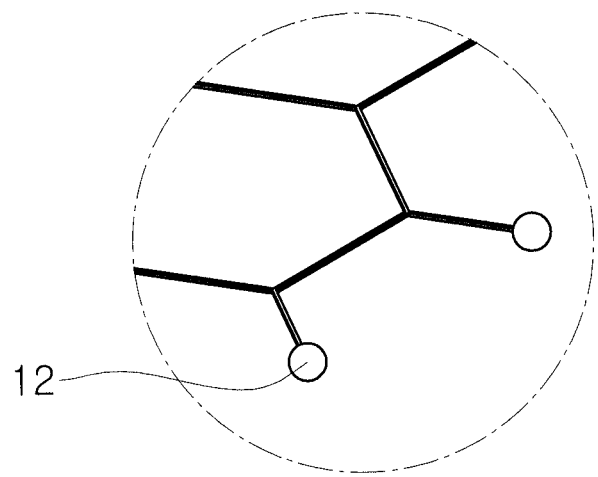
Figure 2:
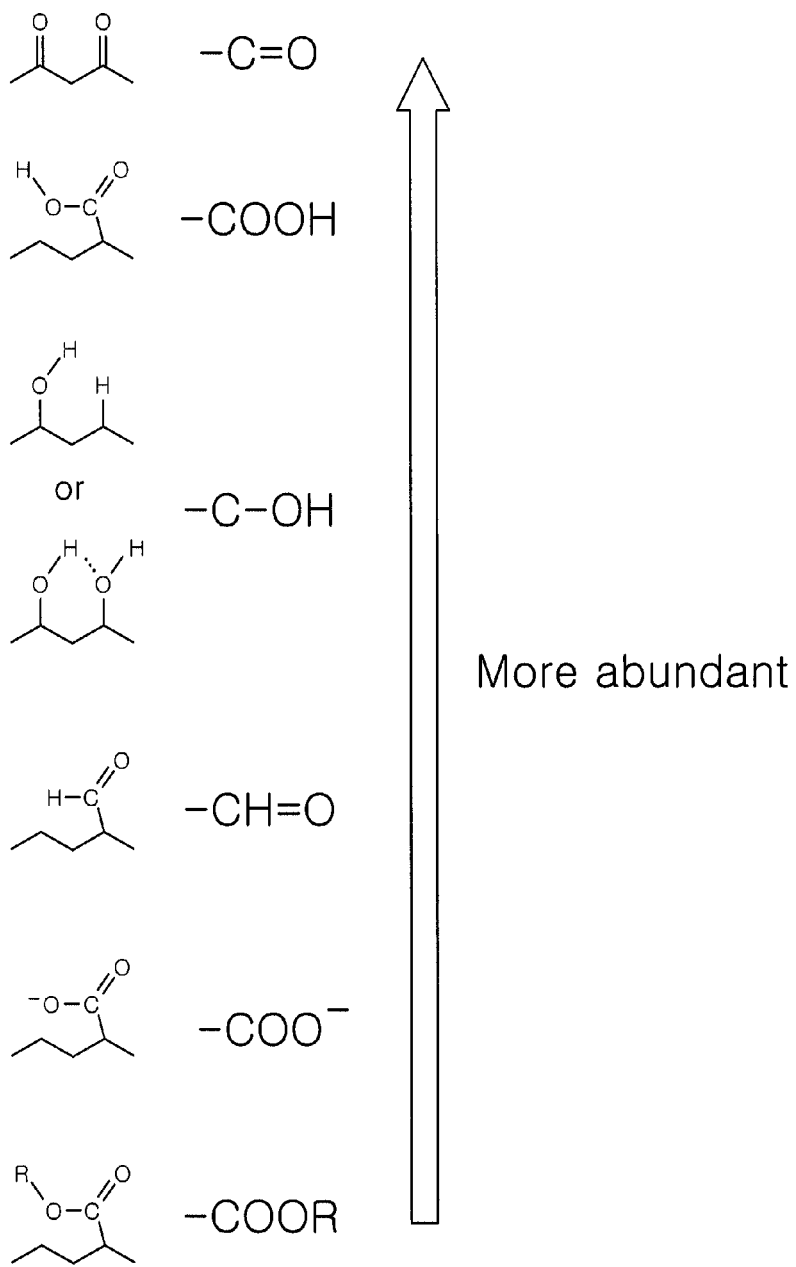
FIG. 2 shows chemical formulas of an exemplary embodiment of a modified graphene edge.

As shown in FIG. 1f, a functional group 12 is introduced at the edge portion. FIG. 2 shows chemical formulas of the functional groups that may be introduced at the chemically modified graphene edge according to an exemplary embodiment.

At the etched graphene edge, a functional group, including —C=O, —COOH, —C—OH, —CH=O, —COO$^-$, —COOR, or the like or a combination thereof, may be introduced by contacting the graphene with the composition comprising hydroxide ions. That is, in an embodiment, the graphene edge may be modified with a carbonyl, carboxyl, hydroxyl, aldehyde, carboxylate or ester functional group, or a combination thereof. The hydroxyl group can be a primary, secondary or tertiary hydroxyl group. As shown in FIG. 2, in an embodiment —C=O is the most abundant among the introduced functional groups, followed by —COOH, —C—OH, —CH=O, —COO$^-$ and —COOR, wherein R represents $C_1$-$C_6$ alkyl, e.g. —$CH_3$, —$C_2H_5$, or the like. In an embodiment, R is a methyl group or an ethyl group.

After the graphene edge portion is chemically modified, the chemically modified graphene has different electrical properties than the electrical properties of the unmodified graphene. Therefore the electrical properties of graphene, including metallic or semiconductor characteristics, electrical resistance, band gap, work function, or the like, may be varied by the chemical modification.

The graphene having modified electrical properties may be desirably used for various devices, such as sensors, FETs or the like.

The Examples, Comparative Examples and experiments will now be further described. The following Examples, Comparative Examples and experiments are for illustrative purposes only and not intended to limit the scope of the present invention.

EXAMPLE 1 AND COMPARATIVE EXAMPLES 1 AND 2

In Example 1, graphene is etched and a functional group is introduced at its edge. In Comparative Example 1, graphene is neither etched nor is a functional group introduced at its edge. In Comparative Example 2, graphene is etched only, without introducing functional group at its edge.

First, a graphene sheet is prepared (see FIG. 1a). The graphene sheet is prepared as follows.

On a 5 centimeter (cm)×5 cm silicon substrate, $SiO_2$ (300 nm) and Ni (300 nm) are sequentially coated to form a support for growth of graphene. The substrate is loaded into a quartz tube furnace. In order to remove an oxide film from the Ni surface, $H_2$ and Ar are supplied at a rate of 100 sccm and 200 sccm, respectively, at 1,100° C. for 1 hour. Then, $CH_4$, $H_2$ and Ar are supplied at a rate of 50 sccm, 65 sccm and 200 sccm, respectively, for 20 minutes, while maintaining the same temperature. Subsequently, the substrate is cooled at a rate of 10 degrees centigrade per second (° C./sec) while supplying Ar at a rate of 200 sccm. Through this CVD process, a graphene sheet is formed on the Ni catalyst. The resultant sample is denoted as an Si/$SiO_2$/Ni/graphene sheet. The Si/$SiO_2$/Ni/graphene sheet sample is immersed in 1 molar (M) $FeCl_3$ aqueous solution to etch Ni. A graphene sheet floating on the aqueous $FeCl_3$ solution is obtained. In Comparative Example 1, the obtained graphene sheet is used without further etching or chemical modification at the edge.

An etching mask is placed on the graphene (refer to FIG. 1b) and oxygen plasma etching is carried out. The graphene, on which the etching mask is placed, is loaded into a chamber and exposed to oxygen gas at 20 sccm under 50 mTorr. Etching is carried out for an exposure time of 30 seconds while applying an electric power of 30 W.

After the etching, the mask is removed from the graphene to obtain a graphene ribbon having an etched edge (refer to FIG. 1c). In Comparative Example 2, the obtained graphene sheet is used without further chemical modification at the edge.

The graphene ribbon is kept in an airtight space and the edge portion is contacted with water by supplying steam. The contacting with steam may be for a time of about 1 minute to 1 hour. The contacting with steam may be at a temperature of about 25° C. to 100° C. The graphene for Example 1, with the edge portion chemically modified, is thus obtained (refer to FIGS. 1d, 1e and 1f).

FT-IR Analysis

Fourier transform infrared spectroscopy ("FT-IR") analysis is carried out on the graphenes of Example 1 and the Comparative Examples.

Figure 3:
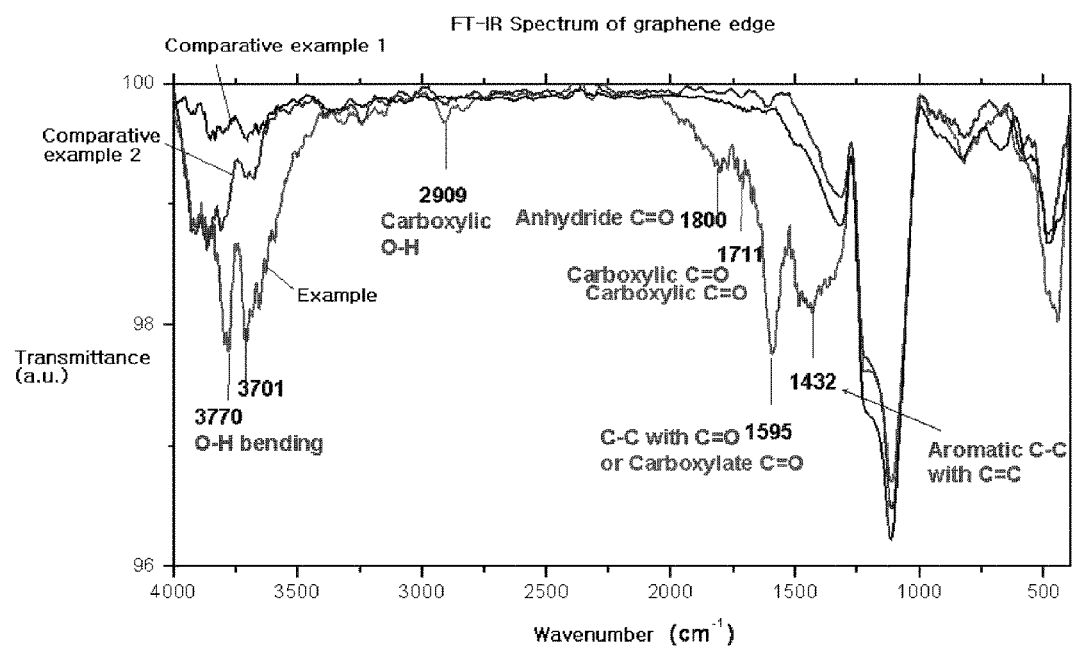
FIG. 3 is a graph illustrating FT-IR spectrums of graphene edges in a graph of transmittance (arbitrary units, a.u.) versus wave number (inverse centimeters, $cm^{-1}$) in accordance with Example 1 and Comparative Examples 1 and 2.

FIG. 3 shows FT-IR spectrums of the graphenes of Example 1 and the Comparative Examples in a graph of transmittance (arbitrary units, a.u.) versus wave number (inverse centimeters, cm$^{-1}$).

Referring to FIG. 3, various functional groups are introduced at the edge portion where the edge portion is contacted with water, in contrast with Comparative Example 1, where neither etching nor introduction of a functional group is included, or Comparative Example 2, where only etching is performed.

The FT-IR analysis for the graphene of Example 1 demonstrates the presence of various functional groups at the edge portion, in addition to C—H bonding. Resonances observed from functional groups include those such as O—H about 3770 cm$^{-1}$ and 3771 cm$^-$, carboxylic O—H at about 2909 cm$^{-1}$, carboxylic C═O at about 1711 cm$^{-1}$, anhydride C═O at about 1800 cm$^{-1}$, and C—C bonded to C═O or carboxylate C═O (i.e., —COO$^-$) at about 1595 cm$^{-1}$.

While the invention has been shown and described with reference to certain exemplary embodiments thereof, it will be understood by those skilled in the art that various changes in form and details may be made thereto without departing from the spirit and scope of the invention as defined by the appended claims.

In addition, modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. Graphene, consisting of:
a single layer of graphene in a thickness direction; and
a functional group disposed on an edge of the graphene, wherein the functional group comprises
═O, and
—CH═O, —COOR wherein R in —COOR represents C$_1$-C$_6$ alkyl, or a combination thereof,
wherein a content of the ═O group is greater than a content of each of the —CH═O group if present and the —COOR group if present.

2. The graphene according to claim 1, wherein the functional group is a product of contacting with water, alcohol or a combination thereof.

3. The graphene according to claim 1, wherein the functional group is a product of contacting with steam.

4. The graphene according to claim 1, wherein the graphene is a graphene sheet formed of polycyclic aromatic molecules with covalently bonded carbon atoms, and further wherein the graphene sheet comprises dimensions of greater than or equal to about 1 mm along each of a transverse direction and a longitudinal direction.

5. The graphene according to claim 1, wherein the functional group comprises —COOR, wherein R represents C$_1$-C$_6$ alkyl.

6. A device comprising graphene, wherein the graphene consists of:
a single layer of the graphene in a thickness direction; and
a functional group disposed on an edge of the graphene, wherein the functional group comprises
═O, and
—CH═O, —COOR wherein R represents C$_1$-C$_6$ alkyl, and a combination thereof,
wherein a content of the ═O group is greater than a content of each of the —CH═O group if present and the —COOR group if present.

7. The graphene according to claim 1, wherein the functional group comprises —CH═O.

* * * * *